(12) United States Patent
Bonrath et al.

(10) Patent No.: US 8,809,591 B2
(45) Date of Patent: Aug. 19, 2014

(54) PROCESS FOR THE MANUFACTURE OF TMHQ

(75) Inventors: Werner Bonrath, Kaiseraugst (CH); Thomas Netscher, Kaiseraugst (CH); Jan Schütz, Kaiseraugst (CH); Bettina Wüstenberg, Kaiseraugst (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/817,012

(22) PCT Filed: Aug. 25, 2011

(86) PCT No.: PCT/EP2011/064623
§ 371 (c)(1),
(2), (4) Date: Apr. 29, 2013

(87) PCT Pub. No.: WO2012/025587
PCT Pub. Date: Mar. 1, 2012

(65) Prior Publication Data
US 2013/0211080 A1    Aug. 15, 2013

(30) Foreign Application Priority Data
Aug. 26, 2010   (EP) .................... 10174083

(51) Int. Cl.
*C07C 45/62* (2006.01)
*C07C 45/65* (2006.01)
*C07C 215/50* (2006.01)
*C07C 225/00* (2006.01)
*C07D 295/116* (2006.01)
*C07D 311/04* (2006.01)

(52) U.S. Cl.
USPC ........... 568/312; 568/313; 564/396; 564/443; 549/411; 548/578; 544/173; 544/398

(58) Field of Classification Search
USPC ........... 568/312, 313; 564/396, 443; 549/411; 548/578; 544/173, 398
See application file for complete search history.

(56) References Cited

U.S. PATENT DOCUMENTS
6,066,731 A    5/2000 Muller et al.

FOREIGN PATENT DOCUMENTS
JP    2006/249036    9/2006

OTHER PUBLICATIONS
International Search Report for PCT/EP2011/064623 mailed Dec. 5, 2011.
K. Sato et al., "Synthesis of Trimethylhydroquinone", Journal of Organic Chemistry, pp. 1928-1929, Jul. 1963.

*Primary Examiner* — Sikarl Witherspoon
(74) *Attorney, Agent, or Firm* — Nixon & Vanderhye P.C.

(57) ABSTRACT

The present invention is directed to a process for the manufacture of 2,3,5-trimethyl-hydro-p-benzoquinone comprising the following steps: a) hydrogenating 2,6-dimethyl-p-benzoquinone with hydrogen in the presence of a hydrogenation catalyst in an organic solvent to obtain 2,6-dimethyl-hydro-p-benzoquinone; b) reacting 2,6-dimethyl-hydro-p-benzoquinone with a secondary amine and formal-dehyde in an organic solvent to obtain 2,6-dimethyl-3-(N,N-disubstituted aminomethyl)-hydro-p-benzoquinone; c) reacting 2,6-dimethyl-3-(N,N-disubstituted aminomethyl)-hydro-p-benzoquinone with hydrogen in the presence of a hydrogenolysis catalyst in an organic solvent to obtain 2,3,5-trimethylhydro-p-benzoquinone; wherein the organic solvent in all steps a), b) and c) is independently selected from the group consisting of methyl tert.-butyl ether, ethyl tert.-butyl ether, methyl tert.-amyl ether, methoxycyclopentane and any mixtures thereof. Preferably the organic solvent used in all steps a), b) and c) is the same.

21 Claims, 3 Drawing Sheets

PROCESS FOR THE MANUFACTURE OF TMHQ

This application is the U.S. national phase of International Application No. PCT/EP2011/064623 filed 25 Aug. 2011 which designated the U.S. and claims priority to EP 10174083.5 filed 26 Aug. 2010, the entire contents of each of which are hereby incorporated by reference.

BACKGROUND AND SUMMARY

As is known, (all-rac)-α-tocopherol (or as it has mostly been denoted in the prior art, "d,l-α-tocopherol") is a mixture of four diastereomeric pairs of enantiomers of 2,5,7,8-tetramethyl-2-(4',8',12'-trimethyl-tridecyl)-6-chromanol (α-tocopherol), which is the biologically most active and industrially most important member of the vitamin E group.

Many processes for the manufacture of "d,l-α-tocopherol" (referred to as such in the literature reviewed hereinafter) by the reaction of 2,3,5-trimethyl-hydro-p-benzoquinone (TMHQ) with isophytol or phytol in the presence of a catalyst or catalyst system and in a solvent or solvent system are described in literature.

One raw material for the production of 2,3,6-trimethylphenol ("2,3,6-TMP", starting material for TMHQ) is m-cresol. Due to limited availability and an increasing demand for m-cresol, prices for m-cresol and 2,3,6-TMP are growing. Therefore a m-cresol-independent access to TMHQ is strongly desired.

One option for a m-cresol free access to TMHQ could be a reaction sequence starting from 2,6-dimethyl-p-benzoquinone ("2,6-DMQ").

The hydrogenation of 2,6-DMQ to 2,6-dimethyl-hydro-p-benzoquinone ("2,6-DMHQ") is a literature-known reaction. There are procedures, using stoichiometric reducing agents such as sodium dithionite [$Na_2(S_2O_4)$] in different solvents (see Carpino, Louis A.; Triolo, Salvatore A.; Berglund, Richard A.; J. Org. Chem. 1989, 54(14), 3303-3310; He, Li; Zhu, Chenjiang; He, Xiaopeng; Tang, Yanhui; Chen, Guorong; Zhongguo Yiyao Gongye Zazhi 2006, 37(5), 301-302; and CN 1 699 356 A).

Modern syntheses describe catalytic hydrogenations using hydrogen in presence of a heterogeneous catalyst [e.g. Pd-catalyst, methanol, room temperature] as claimed in AU 2004 201 149 A1.

The closest state of the art for a reaction sequence from DMQ to TMHQ (see FIG. 1) is disclosed in JP 2006-249 036.

In this reaction sequence each of the three reaction steps is carried out in a different solvent: For the hydrogenation of 2,6-DMQ to 2,6-DMHQ alcohols (iso-propanol), alkyl esters (butyl acetate) or ethers (diethyl ether) are claimed as solvents. The aminomethylation of 2,6-DMHQ is carried out in aromatic hydrocarbons, such as toluene, benzene, ethylbenzene or xylene. And the final de-amination is described in lower aliphatic alcohols (methanol, iso-propanol), alkyl esters (butyl acetate) or ethers (tetrahydrofuran, dioxane). This procedure requires not only the use of various solvents but also the technical operations for two to three solvent changes (distillation).

To by-pass the disadvantage of solvent changes and to achieve high selectivity and yield, it was investigated to carry out as many steps as possible of the reaction sequence from 2,6-DMQ to TMHQ in the same solvent. It was further investigated to find solvents especially suitable for such reaction steps. MTBE (methyl tert.-butyl ether), methoxycyclopentane, ethyl tert.-butyl ether (ETBE) and tert.-amyl methyl ether were found as being especially suitable for the purpose of the present invention. MTBE, ETBE and methoxycyclopentane have the further advantage from an economical point of view that they are cheap. ETBE e.g. is used as antiknock agent for biodiesel. MTBE has the further advantage that it would simplify the work-up because it does not form peroxides.

Disadvantages of the processes known from the prior art are also that larger amounts of bis-Mannich adducts such as e.g. 3,5-dimethyl-2,6-bismorpholinomethyl-hydro-p-benzoquinone are formed as by-products. These by-products have to be removed before TMHQ can be further reacted with isophytol and/or phytol and/or derivatives of isophytol or phytol to vitamin E, because the further reaction products are much more difficult to remove than the bis-Mannich adducts themselves. Advantageously these bis-Mannich adducts are formed in a much lower amount when using the solvents according to the present invention.

Thus, the present invention is directed to a process for the manufacture of 2,3,5-tri-methyl-hydro-p-benzoquinone comprising the following steps:
  a) hydrogenating 2,6-dimethyl-p-benzoquinone with hydrogen in the presence of a hydrogenation catalyst in an organic solvent to obtain 2,6-dimethyl-hydro-p-benzoquinone;
  b) reacting 2,6-dimethyl-hydro-p-benzoquinone with a secondary amine and formaldehyde in an organic solvent to obtain 2,6-dimethyl-3-(N,N-disubstituted aminomethyl)-hydro-p-benzoquinone;
  c) reacting 2,6-dimethyl-3-(N,N-disubstituted aminomethyl)-hydro-p-benzoquinone with hydrogen in the presence of a hydrogenolysis catalyst in an organic solvent to obtain 2,3,5-trimethyl-hydro-p-benzoquinone;
  wherein the organic solvent in all steps a), b) and c) is independently selected from the group consisting of methyl tert.-butyl ether, ethyl tert.-butyl ether, methyl tert.-amyl ether, methoxycyclopentane and any mixtures thereof.

Preferably the organic solvent in all steps a), b) and c) is the same. More preferably this organic solvent is methyl tert.-butyl ether.

Since the obtained 2,3,5-trimethyl-hydro-p-benzoquinone can be further reacted with isophytol and/or phytol and/or derivatives of isophytol or phytol vitamin E, the present invention is also directed to
a process for the manufacture of vitamin E comprising at least one of the steps a) to c) according to the process of the present invention to obtain 2,3,5-trimethyl-hydro-p-benzoquinone which is further reacted with isophytol and/or phytol and/or derivatives of isophytol or phytol vitamin E according to processes known to the person skilled in the art.

Since 2,3,5-trimethyl-hydro-p-benzoquinone may first be converted to 2,3,5-trimethyl-hydro-p-benzoquinone acetate before this 2,3,5-trimethyl-hydro-p-benzoquinone acetate is reacted with isophytol and/or phytol and/or derivatives of isophytol or phytol to vitamin E acetate according to processes known to the person skilled in the art, the present invention is furthermore also directed to
a process for the manufacture of vitamin E acetate comprising at least one of the steps a) to c) according to the process of the present invention to obtain 2,3,5-trimethyl-hydro-p-benzoquinone, which is then converted to 2,3,5-trimethyl-hydro-p-benzoquinone acetate, which is further reacted with isophytol and/or phytol and/or derivatives of isophytol or phytol to vitamin E.

Since the single steps have not been described using these solvents before, the present invention is also directed to a process for the manufacture of 2,6-dimethyl-hydro-p-benzoquinone comprising the step of hydrogenating 2,6-dimethyl-p-benzoquinone with hydrogen in the presence of a hydrogenation catalyst in an organic solvent, wherein the organic solvent is selected from the group consisting of methyl tert.-butyl ether, ethyl tert.-butyl ether, methyl tert.-amyl ether, methoxycyclopentane and any mixtures thereof;

a process for the manufacture of 2,6-dimethyl-3-(N,N-disubstituted aminomethyl)-hydro-p-benzoquinone (preferably of 2,6-dimethyl-3-morpholinomethyl-hydro-p-benzoquinone) comprising the step of reacting 2,6-dimethyl-hydro-p-benzoquinone with a secondary amine (preferably with morpholine) and formaldehyde in an organic solvent to obtain 2,6-dimethyl-3-(N,N-disubstituted aminomethyl)-hydro-p-benzoquinone (preferably 2,6-dimethyl-3-morpholinomethyl-hydro-p-benzoquinone), wherein the organic solvent is selected from the group consisting of methyl tert.-butyl ether, ethyl tert.-butyl ether, methyl tert.-amyl ether, methoxycyclopentane and any mixtures thereof;

a process for the manufacture of 2,3,5-trimethyl-hydro-p-benzoquinone comprising the step of reacting 2,6-dimethyl-3-(N,N-disubstituted aminomethyl)-hydro-p-benzoquinone (preferably 2,6-dimethyl-3-morpholinomethyl-hydro-p-benzoquinone) with hydrogen in the presence of a hydrogenolysis catalyst in an organic solvent to obtain 2,3,5-trimethyl-hydro-p-benzoquinone, wherein the organic solvent is selected from the group consisting of methyl tert.-butyl ether, ethyl tert.-butyl ether, methyl tert.-amyl ether, methoxycyclopentane and any mixtures thereof;

as well as to processes, where two of the three steps are carried out in these solvents, i.e. to a process for the manufacture of 2,6-dimethyl-3-(N,N-disubstituted aminomethyl)-hydro-p-benzoquinone (preferably 2,6-dimethyl-3-morpholinomethyl-hydro-p-benzoquinone) comprising the following steps:

hydrogenating 2,6-dimethyl-p-benzoquinone with hydrogen in the presence of a hydrogenation catalyst in an organic solvent to obtain 2,6-dimethyl-hydro-p-benzoquinone;

reacting 2,6-dimethyl-hydro-p-benzoquinone with a secondary amine (preferably with morpholine) and formaldehyde in an organic solvent to obtain 2,6-dimethyl-3-(N,N-disubstituted aminomethyl)-hydro-p-benzoquinone (preferably 2,6-dimethyl-3-morpholinomethyl-hydro-p-benzoquinone);

wherein the organic solvent is independently selected from the group consisting of methyl tert.-butyl ether, ethyl tert.-butyl ether, methyl tert.-amyl ether, methoxycyclopentane and any mixtures thereof;

a process for the manufacture of 2,3,5-trimethyl-hydro-p-benzoquinone comprising the following steps:

i) reacting 2,6-dimethyl-hydro-p-benzoquinone with a secondary amine (preferably with morpholine) and formaldehyde in an organic solvent to obtain 2,6-dimethyl-3-(N,N-disubstituted aminomethyl)-hydro-p-benzoquinone (preferably 2,6-dimethyl-3-morpholinomethyl-hydro-p-benzoquinone);

ii) reacting 2,6-dimethyl-3-(N,N-disubstituted aminomethyl)-hydro-p-benzoquinone (preferably 2,6-dimethyl-3-morpholinomethyl-hydro-p-benzoquinone) with hydrogen in the presence of a hydrogenolysis catalyst in an organic solvent to obtain 2,3,5-trimethyl-hydro-p-benzoquinone, wherein the organic solvent used in steps i) and ii) is independently selected from the group consisting of methyl tert.-butyl ether, ethyl tert.-butyl ether, methyl tert.-amyl ether, methoxycyclopentane and any mixtures thereof;

a process for the manufacture of 2,3,5-trimethyl-hydro-p-benzoquinone comprising the following steps:

a) hydrogenating 2,6-dimethyl-p-benzoquinone with hydrogen in the presence of a hydrogenation catalyst in an organic solvent to obtain 2,6-dimethyl-hydro-p-benzoquinone;

b) reacting 2,6-dimethyl-hydro-p-benzoquinone with a secondary amine (preferably with morpholine) and formaldehyde in an organic solvent to obtain 2,6-dimethyl-3-(N,N-disubstituted aminomethyl)-hydro-p-benzoquinone (preferably 2,6-dimethyl-3-morpholinomethyl-hydro-p-benzoquinone);

c) reacting 2,6-dimethyl-3-(N,N-disubstituted aminomethyl)-hydro-p-benzoquinone (preferably 2,6-dimethyl-3-morpholinomethyl-hydro-p-benzoquinone) with hydrogen in the presence of a hydrogenolysis catalyst in an organic solvent to obtain 2,3,5-trimethyl-hydro-p-benzoquinone;

wherein the organic solvent in steps a) and c) is independently selected from the group consisting of methyl tert.-butyl ether, ethyl tert.-butyl ether, methyl tert.-amyl ether, methoxycyclopentane and any mixtures thereof.

Also here preferably the organic solvent is the same in two steps. More preferably this organic solvent is methyl tert.-butyl ether.

DETAILED DESCRIPTION

Figure 1:
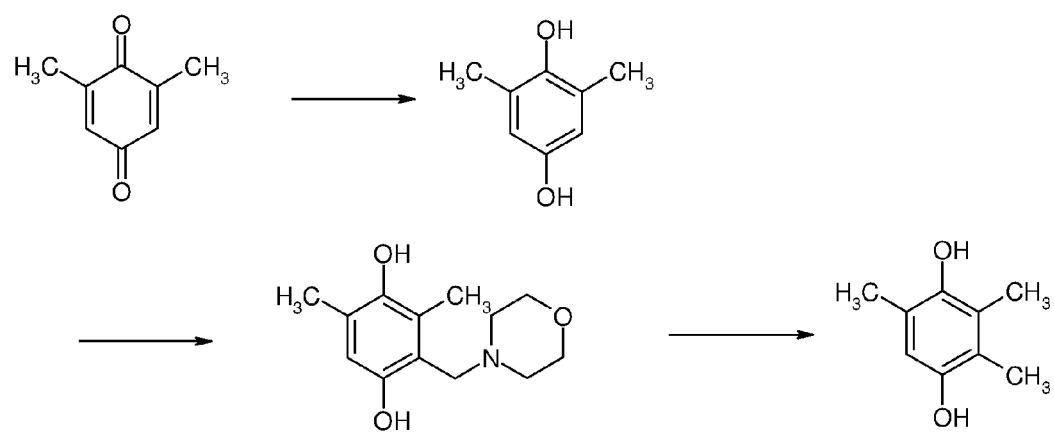
FIG. 1 is a prior art reaction sequence to obtain TMHQ from DMQ.

The single steps are now described in more detail below.

Main advantage of the present invention is that all steps a) to c) may be performed in the same solvent, so that a solvent change is not necessary. It is even not necessary to separate the product of step a) and step b) from the solvent used; it can, however, be optionally done.

In step b) the excess of the Mannich reagents can be separated off and reused. This is important for recycling on a larger scale and is done during work-up. For the work-up, one possibility is an aqueous work-up, the second one is a distillation, as described in U.S. Pat. No. 6,066,731, whose content is included herein by reference; see especially column 5, line 8 ff. and example 6 of U.S. Pat. No. 6,066,731. The distillation of the components off the Mannich reagent (i.e. secondary amine+formaldehyde) is then preferably coupled to the distillation of the solvent.

Step a) Hydrogenation of 2,6-dimethyl-p-benzoquinone (DMQ) to 2,6-dimethyl-hydro-p-benzoquinone (DMHQ)

The Pd-catalyzed hydrogenation of 2,6-DMQ can surprisingly successfully be carried out in excellent yield in MTBE (methyl tert.-butyl ether), methoxycyclopentane, ethyl tert.-butyl ether (ETBE), tert.-amyl methyl ether and any mixtures thereof, more preferably in MTBE and ETBE and any mixtures thereof.

The amount of solvent used, as well as the purity of the starting material (=DMQ) is not critical. It may even be possible to work in a slurry containing the starting material (=2,6-DMQ), the solvent and the catalyst. Preferably 1 l of solvent is used per 1 to 5 mol of 2,6-DMQ.

Supported noble-metal catalysts from the group of platinum metals are efficient catalysts for the hydrogenation of 2,6-DMQ to 2,6-DMHQ. Preferably the noble metal is Pd or Pt. The catalyst can be supported on carbon or an oxide such as silica and alumina or any mixture thereof, preferably on alumina.

The metal loading can be 1-10 weight-%, preferably 3-6 weight-% on the carrier. The substrate/catalyst ratio (s/c) can be in the range of 20-5'000, preferably 40-1'000.

Noble-metal catalysts supported on carbon have preferably a BET surface area in the range of 800 to 1500 m$^2$/g, more preferably they have a BET surface area in the range of 900-1200 m$^2$/g. Most preferably 50% of the particles of these noble-metal catalysts supported on carbon also have a size ≤20-50 μm (i.e. the so-called particle size D50≤20-50 μm).

The catalysts supported on an oxide such as silica and alumina or any mixture thereof have preferably a BET surface area in the range of 50 to 500 m$^2$/g, more preferably they have a BET surface area in the range of 80 to 300 m$^2$/g, most preferably are egg-shell catalysts with these BET surface areas.

An "egg-shell" catalyst in the context of the present invention is a catalyst where the catalytically active metal (Pd, Pt etc.) has a non-uniform distribution on the support and is located mainly on the shell of such catalyst.

The hydrogenation of 2,6-DMQ can be carried out at 1-120 bara, preferably at 2-15 bara. The reaction proceeds faster (<1 hour) under a hydrogen pressure of 3 or 6 bara but it can also be performed at atmospheric pressure, however, with longer reaction times; e.g. with reaction times of 16 to 20 hours with 5% Pd/C (s/c 100) at 23 or 40° C.

Good mixing of the reaction system is crucial for by-passing mass transport limitation.

The reaction can be carried out at a temperature in the range of 0 to 150° C., preferably at a temperature in the range of 10 to 90° C., especially preferred are temperatures in the range of 20 to 70° C.

Step b) Manufacture of the Mannich Adduct of 2,6-dimethyl-hydro-p-benzoquinone Preferably step b) is carried out in the same solvent as step a).

The following solvents are used: MTBE (methyl tert.-butyl ether), methoxycyclopentane, ethyl tert.-butyl ether (ETBE), tert.-amyl methyl ether and any mixtures thereof, preferably MTBE and tert.-amyl methyl ether and any mixtures thereof.

The amount of solvent preferably used is 1 l per 1-5 mol of 2,6-DMHQ, more preferably 1 l per 1-10 mol of 2,6-DMHQ.

Suitable secondary amines are N,N-disubstituted amines L-N(H)-L$^1$, where L and L$^1$ are independently from each other aliphatic linear alkyl groups which may optionally contain heteroatoms such as O and N, aliphatic branched alkyl groups which may optionally contain heteroatoms such as O and N, aryl groups which may optionally contain heteroatoms such as O and N, or L and L$^1$ may form an aliphatic N-containing cycloalkane which may optionally contain further heteroatoms such as O and N.

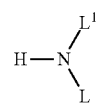

Examples of secondary amines, where L and L$^1$ are independently from each other aliphatic linear alkyl groups which may optionally contain heteroatoms such as O and N, are

- secondary amines, where L and L$^1$ are independently from each other aliphatic linear C$_{1-10}$ alkyl groups (preferably C$_{1-6}$ alkyl groups);
- secondary amines, where L and L$^1$ are independently from each other aliphatic linear C$_{1-10}$ alkyl groups (preferably C$_{1-6}$ alkyl groups) which contain one or more hydroxy groups (preferably they contain one hydroxy group); these hydroxy groups may be tertiary, secondary or primary hydroxy groups;
- secondary amines, where L is an aliphatic linear C$_{1-10}$ alkyl group (preferably a C$_{1-6}$ alkyl group), and L$^1$ is an aliphatic linear C$_{1-10}$ alkyl group (preferably a C$_{1-6}$ alkyl group) which contains one or more hydroxy groups (preferably it contains one hydroxy group); or vice versa; these hydroxy groups may be tertiary, secondary or primary hydroxy groups;
- secondary amines, where L and L$^1$ are independently from each other aliphatic linear C$_{1-10}$ alkyl groups (preferably C$_{1-6}$ alkyl groups) which contain one or more amino groups (preferably they contain one amino group); these amino groups may be tertiary, secondary or primary amino groups;
- secondary amines, where L is an aliphatic linear C$_{1-10}$ alkyl group (preferably a C$_{1-6}$ alkyl group), and L$^1$ is an aliphatic linear C$_{1-10}$ alkyl group (preferably a C$_{1-6}$ alkyl group) which contains one or more amino groups (preferably it contains one amino group); or vice versa; these amino groups may be tertiary, secondary or primary amino groups;
- secondary amines, where L is an aliphatic linear C$_{1-10}$ alkyl group (preferably a C$_{1-6}$ alkyl group) which contains one or more hydroxy groups (preferably it contains one hydroxy group), and L$^1$ is an aliphatic linear C$_{1-10}$ alkyl group (preferably a C$_{1-6}$ alkyl group) which contains one or more amino groups (preferably it contains one amino group); or vice versa; these amino groups may be tertiary, secondary or primary amino groups;
- secondary amines, where L and L$^1$ are independently from each other aliphatic linear C$_{1-10}$ alkyl groups (preferably C$_{1-6}$ alkyl groups) which contain one or more (preferably one) amino and one or more (preferably one) hydroxy groups; these amino and hydroxy groups may be independently from each other tertiary, secondary or primary; as partially illustrated in schemes 1, 2 and 3 below:

Scheme 1

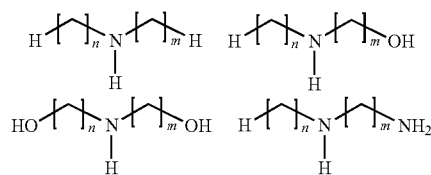

-continued

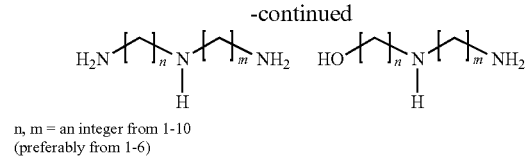

n, m = an integer from 1-10
(preferably from 1-6)

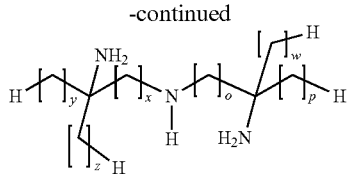

m; x + y + z; o + p + w = an integer from 1-10
(preferably from 1-6)

Scheme 2

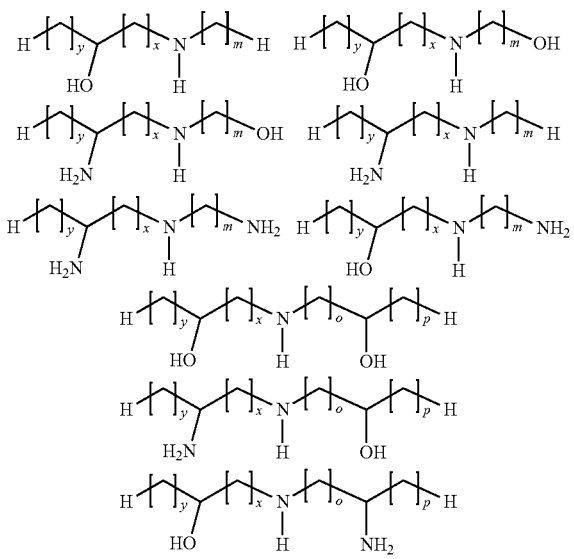

m; x + y; o + p = an integer from 1-10
(preferably from 1-6)

Scheme 3

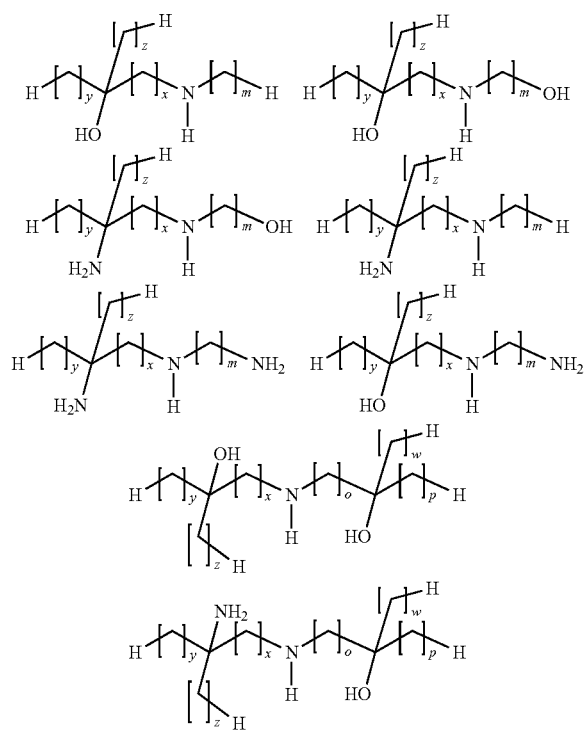

Preferred examples of such secondary amines are dimethyl amine, diethyl amine, diethanol amine and di-n-propyl amine.

Examples of secondary amines, where L and $L^1$ are independently from each other aliphatic branched alkyl groups which may optionally contain heteroatoms such as O and N, are secondary amines, where L and $L^1$ are independently from each other aliphatic branched $C_{3-10}$ alkyl groups (preferably $C_{3-6}$ alkyl groups);

secondary amines, where L and $L^1$ are independently from each other aliphatic branched $C_{3-10}$ alkyl groups (preferably $C_{3-6}$ alkyl groups) which contain one or more hydroxy groups (preferably they contain one hydroxy group); these hydroxy groups may be tertiary, secondary or primary hydroxy groups;

secondary amines, where L is an aliphatic branched $C_{3-10}$ alkyl group (preferably a $C_{3-6}$ alkyl group), and $L^1$ is an aliphatic branched $C_{3-10}$ alkyl group (preferably a $C_{3-6}$ alkyl group) which contains one or more hydroxy groups (preferably it contains one hydroxy group); or vice versa; these hydroxy groups may be tertiary, secondary or primary hydroxy groups;

secondary amines, where L and $L^1$ are independently from each other aliphatic branched $C_{3-10}$ alkyl groups (preferably $C_{3-6}$ alkyl groups) which contain one or more amino groups (preferably they contain one amino group); these amino groups may be tertiary, secondary or primary amino groups;

secondary amines, where L is an aliphatic branched $C_{3-10}$ alkyl group (preferably a $C_{3-6}$ alkyl group), and $L^1$ is an aliphatic branched $C_{3-10}$ alkyl group (preferably a $C_{3-6}$ alkyl group) which contains one or more amino groups (preferably it contains one amino group); or vice versa; these amino groups may be tertiary, secondary or primary amino groups;

secondary amines, where L is an aliphatic branched $C_{3-10}$ alkyl group (preferably a $C_{3-6}$ alkyl group) which contains one or more hydroxy groups (preferably it contains one hydroxy group), and $L^1$ is an aliphatic branched $C_{3-10}$ alkyl group (preferably a $C_{3-6}$ alkyl group) which contains one or more amino groups (preferably it contains one amino group); or vice versa; these hydroxy and amino groups may be tertiary, secondary or primary amino groups;

secondary amines, where L and $L^1$ are independently from each other aliphatic branched $C_{3-10}$ alkyl groups (preferably $C_{3-6}$ alkyl groups) which contain one or more (preferably one) amino and one or more (preferably one) hydroxy groups; these amino and hydroxy groups may be independently from each other tertiary, secondary or primary.

The formulae of these secondary amines are analogous to the ones illustrated in schemes 1 to 3 above.

A preferred example of such secondary amines is di-isopropyl amine.

Examples of secondary amines, where L and L$^1$ may form an aliphatic N-containing cycloalkane which may optionally contain further heteroatoms such as O and N, are piperidine, 1-methyl-piperazine, pyrrolidine and morpholine.

The term "secondary amines" encompasses also N,N-disubstituted amines L-N(H)-L$^1$, where L and L$^1$ are independently from each other single or multiple unsaturated linear alk(mono-/oligo-/poly)enyl groups which may optionally contain heteroatoms such as O and N, single or multiple unsaturated branched alk(mono-/oligo-/poly)enyl groups which may optionally contain heteroatoms such as O and N, or L and L$^1$ may form an aromatic N-containing heterocycle which may optionally contain further heteroatoms such as O and N.

Examples of secondary amines, where L and L$^1$ are independently from each other single or multiple unsaturated linear alk(mono-/oligo-/poly)enyl groups which may optionally contain heteroatoms such as O and N, are secondary amines, where L and L$^1$ are independently from each other single or multiple unsaturated linear C$_{2-10}$ alk(mono-/oligo-/poly)enyl groups (preferably C$_{3-6}$ alk (mono-/oligo-/poly)enyl groups);

secondary amines, where L and L$^1$ are independently from each other single or multiple unsaturated linear C$_{2-10}$ alk(mono-/oligo-/poly)enyl groups (preferably C$_{3-6}$ alk (mono-/oligo-/poly)enyl groups) which contain hydroxy groups; these hydroxy groups may be primary, secondary or tertiary hydroxy groups;

secondary amines, where L and L$^1$ are independently from each other single or multiple unsaturated linear C$_{2-10}$ alk(mono-/oligo-/poly)enyl groups (preferably C$_{3-6}$ alk (mono-/oligo-/poly)enyl groups) which contain amino groups; these amino groups may be primary, secondary or tertiary amino groups;

secondary amines, where L and L$^1$ are independently from each other single or multiple unsaturated linear C$_{2-10}$ alk(mono-/oligo-/poly)enyl groups (preferably C$_{3-6}$ alk (mono-/oligo-/poly)enyl groups) which contain amino and hydroxy groups; these amino and hydroxy groups may be independently from each other primary, secondary or tertiary.

The formulae of these secondary amines are analogous to the ones as illustrated in schemes 1 to 3 above.

Examples of secondary amines, where L and L$^1$ are independently from each other single or multiple unsaturated branched alk(mono-/oligo-/poly)enyl groups which may optionally contain heteroatoms such as O and N, are secondary amines, where L and L$^1$ are independently from each other single or multiple branched linear C$_{3-10}$ alk (mono-/oligo-/poly)enyl groups (preferably C$_{3-6}$ alk (mono-/oligo-/poly)enyl groups);

secondary amines, where L and L$^1$ are independently from each other single or multiple branched linear C$_{3-10}$ alk (mono-/oligo-/poly)enyl groups (preferably C$_{3-6}$ alk (mono-/oligo-/poly)enyl groups) which contain hydroxy groups; these hydroxy groups may be primary, secondary or tertiary hydroxy groups;

secondary amines, where L and L$^1$ are independently from each other single or multiple unsaturated branched C$_{3-10}$ alk(mono-/oligo-/poly)enyl groups (preferably C$_{3-6}$ alk (mono-/oligo-/poly)enyl groups) which contain amino groups; these amino groups may be primary, secondary or tertiary amino groups;

secondary amines, where L and L$^1$ are independently from each other single or multiple unsaturated branched C$_{3-10}$ alk(mono-/oligo-/poly)enyl groups (preferably C$_{3-6}$ alk (mono-/oligo-/poly)enyl groups) which contain amino and hydroxy groups; these amino and hydroxy groups may be independently from each other primary, secondary or tertiary.

The formulae of these secondary amines are analogous to the ones as illustrated in schemes 1 to 3 above.

Examples of secondary amines, where L and L$^1$ may form an aromatic N-containing heterocycle which may optionally contain further heteroatoms such as O and N, are pyridine, pyrrol and imidazol.

Examples of secondary amines, where L is an aliphatic linear C$_{1-10}$ alkyl group or a branched C$_{3-10}$ alkyl group and L$^1$ is an aryl group which may optionally contain heteroatoms such as O and N, are e.g. N-methyl N-phenyl amine, N-ethyl N-phenyl amine, N-methyl N-pyridyl amine etc.

Figure 3:
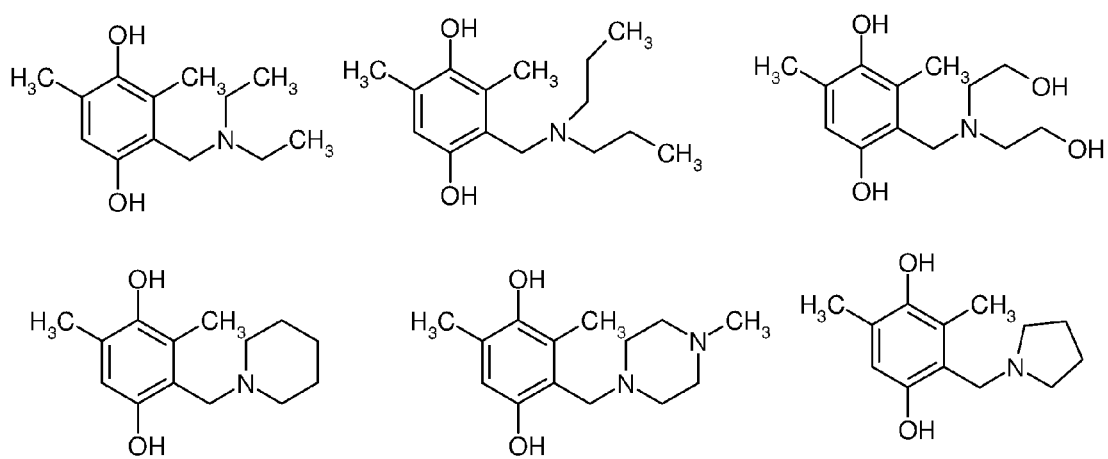
FIG. 3 show the chemical formulas for Mannich adducts of dimethyl amine, diethyl amine, di-n-propyl amine, diethanol amine, piperidine, 1-methyl-piperazine, and pyrrolidine.

Preferably the following secondary amines are used (see FIG. 3): dimethyl amine, diethyl amine, di-n-propyl amine, diethanol amine, piperidine, 1-methyl-piperazine, pyrrolidine and morpholine. More preferably morpholine and piperidine are used. Most preferred is morpholine Equivalents of Mannich reagent: 1.0 to 1.5 mol equivalents; a broader range is 0.8 to 2.0 equivalents per 1 mol of 2,6-DMHQ.

The formaldehyde used in step b) may be used in form of gaseous formaldehyde, formalin (=aqueous 37 weight-% formaldehyde solution), trioxane and para-formaldehyde, preferably it is used in form of formalin, i.e. an aqueous 37 weight-% solution. The aqueous formaldehyde solution may also be more concentrated or more diluted than 37 weight-%, its concentration may e.g be in the range of 10 to 50 weight-%, 25-50 weight-%, 35 to 55 weight-% or 35 to 40 weight-%.

The formaldehyde/formalin/para-formaldehyde is preferably used in an amount of 0.7 to 1.2 mol based on 1 mol of the secondary amine, more preferably in an amount of 0.9 to 1.1 mol based on 1 mol of the secondary amine, most preferably in an equimolar amount based on the amount of the secondary amine.

Preferably this step is carried out at a temperature in the range of 20 to 80° C., more preferably at a temperature in the range of 23 to 60° C.

The reaction can be carried out under pressure (N$_2$ atmosphere), but this is usually not necessary since the reaction also proceeds smoothly at atmospheric pressure.

Usually the reaction proceeds in a time in the range of 2 to 48 hours, preferably in the range of 6 to 24 hours.

For more details about this reaction step see U.S. Pat. No. 6,066,731 which content is included herein by reference, especially columns 2 and 3, as well as examples 1-3 and 8. The Mannich reagent can also be pre-formed.

Step c) Hydrogenolysis of 2,6-dimethyl-3-(N,N-disubstituted aminomethyl)-hydro-p-benzoquinone to 2,3,5-trimethyl-hydro-p-benzoquinone Preferably step c) is carried out in the same solvent as step b). More preferably step c) is carried out in the same solvent as step a) and step b).

The following solvents are used: MTBE (methyl tert.-butyl ether), methoxycyclopentane, ethyl tert.-butyl ether (ETBE), tert.-amyl methyl ether and any mixtures thereof, preferably MTBE and tert.-amyl methyl ether and any mixtures thereof.

Usually 1 l of solvent is used per 0.2 to 10 mol of starting material (=disubstituted 2,6-dimethyl-3-(N,N-disubstituted aminomethyl-hydro-p-benzoquinone, preferably 2,6-dimethyl-3-morpholinomethyl-hydro-p-benzoquinone); preferably 1 l of solvent is used per 0.3 to 5 mol of starting material (=disubstituted 2,6-dimethyl-3-(N,N-disubstituted aminomethyl-hydro-p-benzoquinone, preferably 2,6-dimethyl-3-morpholinomethyl-hydro-p-benzoquinone).

Reaction Temperature

The range from 120° C. to 200° C. is preparatively useful, a more specific useful temperature range is 140-180° C.; the most preferred temperature range is 150 to 170° C.

The hydrogen pressure is typically in the range of 5 to 100 bara, preferably in the range of 15 to 55 bara.

The reaction usually proceeds in a time in the range of 2 to 10 hours; preferably the reaction is complete in a time in the range of from 4 to 6 hours.

Supported noble-metal catalysts from the group of platinum metals, as well as nickel are efficient catalysts for this hydrogenolysis. The catalyst can be supported on carbon or an oxide such as silica and alumina or any mixture thereof, as well as on porous glass such as TRISOPERL®.

The catalyst used in step c) is preferably selected from the group consisting of Pd/C, Pd/SiO$_2$, Pd/Al$_2$O$_3$, Pd/TP (TP=TRISOPERL®) and Ra—Ni (=Ni-alloy). More preferred catalysts are Pd/C, Pd/TP and Pd/SiO$_2$. Most preferred catalysts are Pd/C and Pd/TP.

Noble-metal catalysts (especially Pd) supported on carbon have preferably a BET surface area in the range of 800 to 1500 m$^2$/g, more preferably they have a BET surface area in the range of 900-1200 m$^2$/g. Most preferably 50% of the particles of these noble-metal catalysts supported on carbon also have a size ≤20-50 µm (i.e. the so-called particle size D50≤20-50 µm).

The catalysts supported on an oxide such as silica and alumina or any mixture thereof have preferably a BET surface area in the range of 50 to 500 m$^2$/g, more preferably they have a BET surface area in the range of 80 to 300 m$^2$/g. Most preferably are eggshell catalysts.

Preferably the weight ratio of the nobel metal (Pd, Ni) contained in these catalysts to the starting material of this step (=2,6-dimethyl-3-(N,N-disubstituted aminomethyl)-hydro-p-benzoquinone with the preferences as given above) is 1:(20-10000), preferably 1:(50-1000), more preferably around 1:200.

The invention is now further illustrated by the following non-limiting examples.

EXAMPLES

Figure 2:
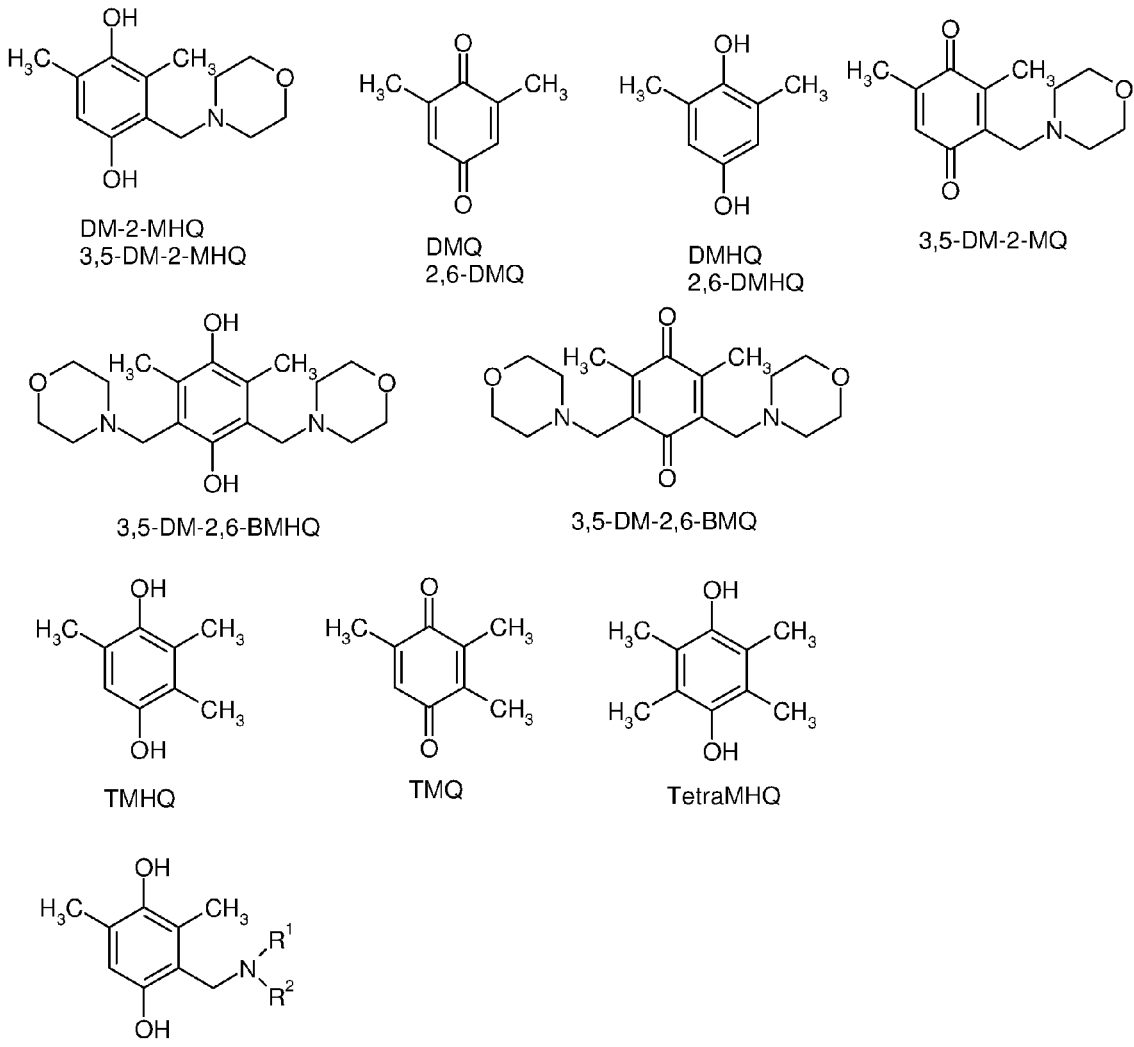
FIG. 2 show the chemical formulas for compounds of the Examples.

The following abbreviations were used (see also FIG. 2):
MTBE=tert.-butyl methyl ether
rpm=revolutions per minute
wt-%=weight-%
DM-2-MHQ=dimethyl-2-morpholinomethyl-quinone
(2,6-)DMQ=2,6-dimethylbenzoquinone (starting material for step a), its purity being not critical)
(2,6-)DMHQ=2,6-dimethyl-hydro-p-benzoquinone
3,5-DM-2-MQ=3,5-dimethyl-2-morpholinomethyl-quinone
3,5-DM-2-MHQ=3,5-dimethyl-2-morpholinomethyl-hydro-p-benzoquinone (=2,6-dimethyl-3-morpholinomethyl-hydro-p-benzoquinone)
3,5-DM-2,6-BMHQ=3,5-dimethyl-2,6-bismorpholinomethyl-hydro-p-benzoquinone
3,5-DM-2,6-BMQ=3,5-dimethyl-2,6-bismorpholinomethyl-p-benzoquinone
TMHQ=2,3,5-trimethyl-hydro-p-benzoquinone
TMQ=2,3,6-trimethylbenzoquinone
TetraMHQ=2,3,5,6-tetramethylhydro-p-benzoquinone
s/c=substrate/catalyst ratio
bara=bar absolute Catalysts:
The following catalysts were used:
a 5% Pd/C catalyst with a BET surface area of 1000 m$^2$/g and the following particle size distribution: 10% of the particles ≤6 µm, 50% of the particles ≤28 µm, and 90% of the particles ≤79 µm, as e.g. commercially available from Evonik under the tradename "Pd/C (5%) E 101 N/D (Evonik)" ("catalyst A");

a 10% Pd/C catalyst with a a BET surface area of 1000 m$^2$/g and a pore volume of 1.1 ml/g, as e.g. commercially available from Evonik under the tradename "Pd/C (10%) E 101 N/D (Evonik)" ("catalyst B");

a 10% Pd/C egg-shell catalyst as e.g. commercially available from Evonik under the tradename "Pd/C (10%): E 101 NN/D (Evonik)" ("catalyst C");

a 5% Pd/SiO$_2$ catalyst with a BET surface area of 275 m$^2$/g, a pore volume of 1.7 ml/g, a volume of mesopores of 0.66 ml/g and a volume of macropores of 1.04 ml/g as e.g. commercially available from Evonik under the tradename "Pd/SiO$_2$ (5%) E EXP/D (Evonik)" ("catalyst D");

a 5% Pd/CaCO$_3$ egg-shell catalyst with a BET surface area of 8 m$^2$/g, a bulk density of 0.37 kg/l, and whereby 50% of the particles have a size ≤5 µm as e.g. commercially available from Evonik under the tradename "5% Pd/CaCO$_3$ E 407 R/D" ("catalyst E");

a 5% Pd/Al$_2$O$_3$ egg-shell catalyst with a BET surface area of 93 m$^2$/g and a pore volume of 0.3 ml/g as e.g. commercially available from Evonik under the tradename "5% Pd/Al$_2$O$_3$ E 213 R/D" ("catalyst F");

a 5% Pt/C catalyst with a BET surface area of 100 m$^2$/g, a volume of the micropores of 0.35 ml/g, a volume of the mesopores of 0.35 ml/g, a volume of the macropores of 0.30 ml/g and a pore volume 1.0 ml/g as e.g. commercially available from Evonik under the tradename "5% Pt/C F 101 R/D" ("catalyst G");

a Raney-Nickel catalyst containing Ni in an amount in the range of 90 to 95 weight-%, based on the total weight of the catalyst, aluminum in an amount in the range of 5.5 to 8 weight-%, based on the total weight of the catalyst, iron in an amount in the range ≤0.4 weight-%, based on the total weight of the catalyst, and the following particle size distribution: 10% of the particles ≤5 to 13 µm, 50% of the particles ≤35 to 70 µm, and 90% of the particles ≤300 µm as e.g. commercially available under the tradename "RaNi MC700 B.2063" ("catalyst H");

a 1% Pd/TP catalyst ("catalyst I") whose manufacture is described below.

1% Pd/TP was Manufactured as Follows:
21 mg Pd(OAc)$_2$ (0.09 mmol) were suspended in 50 mL of dichloromethane. 1 g of TRISOPERL® were added and the solvent was removed (bath temperature: 40° C./pressure: 950 mbara). The carrier doped with Pd(OAc)$_2$ was calcinated for 2 hours at 300° C. in an oven (pre-heating of the oven for 20 minutes for 1000 W to 300° C.). The loading of the catalyst on the carrier was then ca. 1 weight-% Pd, i.e. 10 mg of Pd on 1 g of carrier. TRISOPERL® by the Schuller GmbH, Wertheim/Germany, is a porous Silica glass with an average particle size in the range of 100 to 200 µm, an average pore size of 54.47 nm, a specific surface of 93.72 m$^2$/g and an average pore volume of 1255.5 mm$^3$/g.

Solvents:
Acetonitrile, tert.-amyl methyl ether, tert.-butyl ethyl ether, ethyl acetate, methanol, methoxycyclopentane, tert.-butyl methyl ether, iso-propanol and toluene are all commercially available and were used as such.

2,6-Dimethylhydroquinone, diethanolamine, di-n-propylamine, pyrrolidine, 1-methyl-piperazine, piperidine, morpholine, dimethylamine solution (aq. 40%), and formaldehyde solution (aq. 37%) are commercially available and were used without further purification.

I) Hydrogenation of 2,6-dimethyl-p-benzoquinone (DMQ) to 2,6-dimethyl-hydro-p-benzoquinone (DMHQ)

For the hydrogenation of 2,6-DMQ to 2,6-DMHQ different solvents were tested, with variation of the catalyst (support), hydrogen pressure and temperature. After the reaction, the products were isolated and the purity and yield of DMHQ, based on DMQ, were determined by GC and quantitative $^1$H-NMR.

The results and the reaction conditions and parameters are summarized in the following tables. Some of the experiments are described in more detail below.

TABLE 1

Hydrogenation of DMQ using various solvents (temperature: 40° C., hydrogen pressure: 6 bara, catalyst: 10% Pd/C, s/c: 100).

| Example | time [h] | Solvent | Selectivity [based on GC-area %] | Yield [%] |
|---|---|---|---|---|
| I.1 | 1.5 | MTBE | 94.8 | 88 |
| I.2 | 1.5 | methoxycyclopentane | 93.1 | 85 |
| I.3 | 3.5 | tert.-butyl ethyl ether | 96.3 | 88 |
| I.4 | 2 | tert.-amyl methyl ether | 95.2 | 87 |

Detailed Description of Example I.3

In a 13 ml glass flask flushed with argon (3×6 bara), 275 mg (2.0 mmol) of DMQ were dissolved in 1.63 g (2.2 ml) of tert.-butyl ethyl ether. To the solution 20.0 mg (s/c 100) of Pd/C (10 weight-% Pd, based on the total weight of the catalyst) catalyst were added. The autoclave was flushed with hydrogen and heated to 40° C. with magnetic stirring (500 rpm). When the reaction temperature was reached, the autoclave was pressurized with 6 bara hydrogen and stirring was increased to 1'000 rpm. After 3.5 hours reaction time, the suspension was cooled to 23° C. and the hydrogen pressure was released. The suspension was filtered and the catalyst was washed with 1 ml of MTBE. The combined organic layers were concentrated at 40° C. under reduced pressure. The product was obtained in 88% yield and 91% purity.

TABLE 2

Hydrogenation of DMQ at various hydrogen pressures (temperature: 40° C., solvent: MTBE, catalyst: 10% Pd/C: s/c: 100).

| Example | H$_2$ [bara] | time [h] | Selectivity [based on GC-area %] | Yield [%] |
|---|---|---|---|---|
| I.5 | 6 | 1 | 96.9 | 94 |
| I.6 | 3 | 1 | 95.7 | 94 |
| I.7 | 1 | 20 | 96.2 | 92 |

Investigation of the hydrogen pressure showed that at 6 bara the Pd-catalyzed hydrogenation of 2,6-DMQ is complete with ca. 97% selectivity within 1 hour reaction time at 40° C. A similar result is obtained at 3 bara hydrogen pressure. When carried out at atmospheric pressure, the reaction proceeds slower but 99.6% conversion is achieved after 20 hours with 96.2% selectivity (Table 2).

Detailed Description of Example I.5

In a 30 ml steel autoclave flushed with argon (3×6 bara), 154.2 mg (1.1 mmol) of DMQ were dissolved in 0.82 g (1.1 ml) of MTBE. To the solution 12.4 mg (s/c 100) of Pd/C (10 weight-% Pd, based on the total weight of the catalyst) catalyst were added. The autoclave was flushed with hydrogen and heated to 40° C. with magnetic stirring (500 rpm). When the reaction temperature was reached, the autoclave was pressurized with 6 bara hydrogen and stirring was increased to 1'000 rpm. After 1 hour reaction time, stirring was reduced to 100 rpm, the suspension was cooled to 23° C. and the hydrogen pressure was released. The suspension was filtered via syringe filter (0.45 μm), the catalyst was washed with 5 ml of MTBE and the combined organic layers were concentrated at 40° C. under reduced pressure. The product was obtained in 94% yield and 87% purity.

Detailed Description of Example I.7

In a 50 ml round-bottom flask, 4.6 g (29.8 mmol) of DMQ were dissolved in 33 ml of MTBE under argon atmosphere. To the solution were added 318 mg (s/c 100) of Pd/C (10 weight-% Pd, based on the total weight of the catalyst) catalyst and the argon atmosphere was exchanged with hydrogen (three cycles). After that the reaction mixture was stirred (800 rpm) for 16 hours at 40° C. under hydrogen atmosphere (balloon). The black suspension was filtered and the catalyst washed with 10 ml of MTBE. The organic layer was concentrated at 40° C. under reduced pressure and the solid product was dried for one hour at 40° C. at 15 mbara. The product was obtained in 92% yield and 90% purity.

TABLE 3

Hydrogenation of DMQ at various temperatures (solvent: MTBE)

| Example | Catalyst [s/c] | H$_2$ [bara] | Temperature [° C.] | time [h] | Selectivity [based on GC-area %] | Yield [%] |
|---|---|---|---|---|---|---|
| I.8 | Pd/C (5%) [40] | 6 | 40 | 0.5 | 96.9 | 87 |
| I.9 | Pd/C (5%) [40] | 6 | 23 | 0.5 | 98.2 | 81 |
| I.10 | Pd/C (10%) [100] | 1 | 40 | 20 | 96.2 | 92 |
| I.11 | Pd/C (10%) [100] | 1 | 23 | 16 | 99.5 | 76 |
| I.12 | Pd/C (10%) [100] | 11 | 60 | 16 | 95.7 | 69 |

Compared to the hydrogen pressure, the reaction temperature plays a minor role (Table 3).

TABLE 4

Hydrogenation of DMQ using Pd-catalysts on various supports (temperature: 40° C., hydrogen pressure: 6 bara, solvent: MTBE).

| Example | Catalyst [s/c] | time [h] | Selectivity [based on GC-area %] | Yield [%] |
|---|---|---|---|---|
| I.13 | Pd/C (5%) [40] | 0.5 | 96.9 | 87 |
| I.14 | Pd/C (10%) [100] | 0.5 | 96.5 | 95 |

TABLE 4-continued

Hydrogenation of DMQ using Pd-catalysts on various supports
(temperature: 40° C., hydrogen pressure: 6 bara, solvent: MTBE).

| Example | Catalyst [s/c] | time [h] | Selectivity [based on GC-area %] | Yield [%] |
|---|---|---|---|---|
| I.15 | Pd/SiO$_2$ (5%) [100] | 1.0 | 97.0 | 95 |
| I.16 | Pd/Al$_2$O$_3$ (5%) [100] | 1.0 | 98.2 | 97 |

With Pd/Al$_2$O$_3$ slightly higher yield and selectivity is observed than with Pd/SiO$_2$ or Pd/C (Table 4).

Example I.17

In a 2-liter steel autoclave, 125.7 g (815 mmol) of DMQ were dissolved in 910 ml of tert.-butyl methyl ether (MTBE) under a nitrogen atmosphere at 23° C. To this solution were added 8.64 g (s/c 100) of a Pd/C (10 weight-% Pd, based on the total weight of the catalyst) catalyst. With stirring (gas dispersion stirrer, 1000 rpm) the autoclave was pressurized with hydrogen to 6 bara. During this process the temperature rose to 30° C. After the exothermic reaction had ceased, the reaction mixture was heated to 40° C. After 75 min, the catalyst was filtered off and washed with 140 ml of MTBE. The combined ether layers were concentrated under reduced pressure at 40° C. and the solid crude product was dried for 2 hours at 40° C. The off-white crystalline DMHQ was obtained in 92% yield and 85% purity.

Most reactions were carried out on a 150-300 mg scale. Experiment I.17 demonstrates that the reaction conditions from the screening experiments also apply for a larger laboratory scale (125 g). In this case, the hydrogenation was performed in a 2 liter steel autoclave. To ensure good hydrogen transfer into the solution a gas entrainment stirrer was used. With this set-up the product was obtained in good yield of 92% and 95.6% selectivity.

II) Manufacture of the Mannich Adduct of 2,6-dimethyl-hydro-p-benzoquinone

Example II.1

Aminomethylation in tert.-butyl methyl ether

To a stirred suspension of DMHQ (20.8 g, 99.5 wt-%, 150.0 mmol) in tert.-butyl methyl ether (MTBE, 75 ml) was added under an argon atmosphere the Mannich reagent (26.35 g, 225.0 mmol, 1.5 mol equiv.) prepared from morpholine and paraformaldehyde according to example 1 of U.S. Pat. No. 6,066,731. The resulting brown solution was heated to 60° C. (oil bath temperature 70° C.) for 6 hours. During this time the brown solution turned to a suspension. The reaction mixture was cooled down to 0° C. in an ice bath, the colourless crystals filtered off by suction filtration (P3 frit), washed twice with 10 ml each of cold (0° C.) MTBE, and dried overnight (16 hours) at room temperature under high vacuum. The colourless crystals obtained (31.704 g) were analyzed by quantitative HPLC. The mother liquor was evaporated in vacuo (40° C., 20 mbara), further dried overnight (16 hours) at room temperature under high vacuum. The 11.369 g dark red oil was analyzed by quantitative HPLC.

Yield according to quantitative HPLC (crystals+mother liquor): 91.3% 3,5-DM-2-MHQ, 1.0% 2,6-DMHQ, 0.5% 3,5-DM-2-MQ, 0.0% 2,6-DMQ, 0.0% 3,5-DM-2,6-BMHQ, 0.2% 3,5-DM-2,6-BMQ.

Example II.2

Aminomethylation in tert.-butyl ethyl ether

Carrying out the experiment described in Example II.1 with tert.-butyl ethyl ether as the solvent, the following results were obtained:

Yield according to quantitative HPLC (crystals+mother liquor): 85.1% 3,5-DM-2-MHQ, 0.7% 2,6-DMHQ, 0.4% 3,5-DM-2-MQ, 0.0% 2,6-DMQ, 0.0% 3,5-DM-2,6-BMHQ, 0.7% 3,5-DM-2,6-BMQ.

Example II.3

Aminomethylation in tert.-amyl methyl ether

Carrying out the experiment described in Example II.1 with tert.-amyl methyl ether as the solvent, the following results were obtained:

Yield according to quantitative HPLC (crystals+mother liquor): 89.5% 3,5-DM-2-MHQ, 0.7% 2,6-DMHQ, 1.9% 3,5-DM-2-MQ, 0.0% 2,6-DMQ, 0.0% 3,5-DM-2,6-BMHQ, 1.0% 3,5-DM-2,6-BMQ.

Example II.4

Aminomethylation in methoxycyclopentane

Carrying out the experiment described in Example II.1 with methoxycyclopentane as the solvent, the following results were obtained:

Yield according to quantitative HPLC (crystals+mother liquor): 84.4% 3,5-DM-2-MHQ, 0.6% 2,6-DMHQ, 1.6% 3,5-DM-2-MQ, 0.0% 2,6-DMQ, 0.0% 3,5-DM-2,6-BMHQ, 1.2% 3,5-DM-2,6-BMQ.

Comparison Example II.C1

Aminomethylation in Toluene

To a stirred suspension of 2,6-dimethyl-hydro-p-benzoquinone (0.697 g, 99.1 wt %, 5.0 mmol) in toluene (2.5 ml) was added under an argon atmosphere morpholine (0.528 g, 6.0 mmol, 1.2 mol equiv.). After stirring for 10 minutes a paraformaldehyde solution (37% in H$_2$O, 0.487 g, 6.0 mmol, 1.2 mol equiv. formaldehyde) was added in one portion, and the temperature rose from 23 to 30° C. The resulting brown two-phase mixture was then heated at 55° C. (oil bath temperature 70° C.) for 16 hours. After cooling down to 30° C., 10 ml of H$_2$O and 30 ml of ethyl acetate were added. After phase separation the aqueous layer was extracted with 20 ml of ethyl acetate, and the combined organic extracts dried over sodium sulfate. After filtration and evaporation in vacuo (40° C./20 mbara) and further drying (2 h, high vacuum, room temperature), the resulting 1.136 g red-brown solid was analyzed by quantitative HPLC.

Yield: 70.3% 3,5-DM-2-MHQ, 1.2% 2,6-DMHQ, 4.9% 3,5-DM-2-MQ, 0.1% 2,6-DMQ, 3.1% 3,5-DM-2,6-BMHQ, 0.7% 3,5-DM-2,6-BMQ.

Analytical Data for the Morpholine Mannich Adduct $^1$H-NMR (300 MHz, d$_6$-DMSO): δ=6.35 (s, 1H, CH), 3.55 (t, 4H, J=4.52 Hz, CH$_2$O), 3.53 (s, 2H, Ar—CH$_2$N), 2.40 (br t, 4H, J=4.52 Hz, CH$_2$CH$_2$N), 2.11 (s, 3H, CH$_3$), 2.08 (s, 3H, CH$_3$).

$^{13}$C-NMR (75 MHz, d$_6$-DMSO): δ=149.7 (COH), 145.2 (COH), 125.1 (CCH$_3$), 124.7 (CCH$_3$), 118.2 (CCH$_2$), 114.3 (CH), 66.2 (CH$_2$O), 55.2 (Ar—CH$_2$N), 52.6 (CH$_2$CH$_2$N), 16.8 (CH$_3$), 12.3 (CH$_3$).

LC-MS (ES) m/z: 238 [M+H$^+$], 151 [M+H$^+$-morpholine].

IR (ATR, cm$^{-1}$): 3348 (m, —OH), 3011 (w, Ar—H), 2956, 2933, (m, —CH$_3$, —CH$_2$—CH$_3$, —CH$_2$—), 2848 (m, —NR$_3$), 1470 (m), 1230 (s), 1009 (s).

In an analogous manner the Mannich adducts with piperidine, 1-methyl-piperazine, pyrrolidine, diethanolamine, di-n-propylamine, diethylamine or dimethylamine were synthesized which analytical data are given below.

Analytical Data for the Piperidine Mannich Adduct $^1$H-NMR (300 MHz, d$_6$-DMSO): δ=6.30 (s, 1H, CH), 3.54 (s, 2H, Ar—CH$_2$N), 2.40 (br, 2H, CH$_2$CH$_2$N), 2.07 (s, 6H, CH$_3$), 1.50 (br quin, 4H, CH$_2$CH$_2$N), 1.42 (br t, 2H, CH$_2$CH$_2$CH$_2$N).

$^{13}$C-NMR (75 MHz, d$_6$-DMSO): δ=150.4 (COH), 145.0 (COH), 124.5 (CCH$_3$), 124.2 (CCH$_3$), 118.0 (CCH$_2$), 114.4 (CH), 56.7 (Ar—CH$_2$N), 53.2 (CH$_2$CH$_2$N), 25.5 (CH$_2$CH$_2$N), 23.7 (CH$_2$CH$_2$CH$_2$N), 16.8 (CH$_3$), 12.2 (CH$_3$).

LC-MS (ES) m/z: 236 [M+H$^+$], 151 [M+H$^+$-piperidine].

IR (ATR, cm$^{-1}$): 3348 (m, —OH), 3011 (w, Ar—H), 2956, 2933, (m, —CH$_3$, —CH$_2$—CH$_3$, —CH$_2$—), 2848 (m, —NR$_3$), 1470 (m), 1230 (s), 1009 (s).

Analytical Data for the 1-methyl-piperazine Mannich Adduct $^1$H-NMR (300 MHz, d$_6$-DMSO): δ=6.32 (s, 1H, CH), 3.55 (s, 2H, Ar—CH$_2$N), 2.47-2.22 (br, 8H, NCH$_2$CH$_2$N), 2.15 (s, 3H, CH$_3$), 2.08 (s, 3H, CH$_3$), 2.07 (s, 3H, CH$_3$N).

$^{13}$C-NMR (75 MHz, d$_6$-DMSO): δ=150.0 (COH), 145.1 (COH), 124.6 (CCH$_3$), 124.6 (CCH$_3$), 118.1 (CCH$_2$), 114.4 (CH), 55.4 (Ar—CH$_2$N), 54.7 (NCH$_2$CH$_2$N), 51.9 (NCH$_2$CH$_2$N), 45.6 (NCH$_3$), 16.8 (CH$_3$), 12.3 (CH$_3$).

LC-MS (ES) m/z: 251 [M+H$^+$], 151 [M+H$^+$-1-methyl-piperazine].

Analytical Data for the Pyrrolidine Mannich Adduct $^1$H-NMR (300 MHz, d$_6$-DMSO): δ=6.30 (s, 1H, CH), 3.72 (s, 2H, Ar—CH$_2$N), 2.53 (m, 4H, CH$_2$CH$_2$N), 2.09 (s, 3H, CH$_3$), 2.07 (s, 3H, CH$_3$), 1.72 (m, 4H, CH$_2$CH$_2$N).

$^{13}$C-NMR (75 MHz, d$_6$-DMSO): δ=150.3 (COH), 144.9 (COH), 124.4 (CCH$_3$), 123.9 (CCH$_3$), 119.0 (CCH$_2$), 114.3 (CH), 53.3 (Ar—CH$_2$N), 53.0 (CH$_2$CH$_2$N), 23.2 (CH$_2$CH$_2$N), 16.8 (CH$_3$), 12.2 (CH$_3$).

LC-MS (ES) m/z: 222 [M+H$^+$], 151 [M+H$^+$-pyrrolidine].

Analytical Data for the Diethanolamine Mannich Adduct $^{13}$C-NMR (75 MHz, d$_6$-DMSO): δ=150.5 (COH), 145.0 (COH), 124.5 (CCH$_3$), 124.3 (CCH$_3$), 119.1 (CCH$_2$), 114.5 (CH), 58.4 (HOCH$_2$CH$_2$N or HOCH$_2$CH$_2$N), 55.7 (HOCH$_2$CH$_2$N or HOCH$_2$CH$_2$N), 53.1 (Ar—CH$_2$N), 16.8 (CH$_3$), 12.3 (CH$_3$).

LC-MS (ES) m/z: 256 [M+H$^+$], 151 [M+H$^+$-diethanolamine].

GC-MS (EI) (silylated) m/z: 528 [M$^+$+4 TMS–CH$_3$], 440 [M$^+$+3 TMS–2 CH$_3$] 295 [M$^+$+2 TMS-diethanolamine].

Analytical Data for the Di-n-Propylamine Mannich Adduct $^1$H-NMR (300 MHz, d$_6$-DMSO): δ=6.29 (s, 1H, CH), 3.63 (s, 2H, Ar—CH$_2$N), 2.38 (t, J=7.54 Hz, 4H, CH$_3$CH$_2$CH$_2$N), 2.07 (s, 3H, CH$_3$), 1.45 (m, J=7.35 Hz, J=7.54 Hz, 4H, CH$_3$CH$_2$CH$_2$N), 0.81 (t, J=7.35 Hz, 4H, CH$_3$CH$_2$CH$_2$N).

$^{13}$C-NMR (75 MHz, d$_6$-DMSO): δ=150.6 (COH), 144.9 (COH), 124.4 (CCH$_3$), 124.1 (CCH$_3$), 118.5 (CCH$_2$), 114.4 (CH), 54.9 (CH$_2$CH$_2$CH$_2$N), 53.1 (Ar—CH$_2$N), 19.1 (CH$_2$CH$_2$CH$_2$N), 16.8 (CH$_3$), 12.1 (CH$_3$), 11.7 (CH$_2$CH$_2$CH$_2$N).

GC-MS (EI) (silylated) m/z: 395 [M$^+$+2 TMS], 380 [M$^+$+2 TMS–CH$_3$] 295 [M$^+$+2 TMS–di-n-propylamine].

Analytical Data for the Dimethylamine Mannich Adduct $^1$H-NMR (300 MHz, d$_6$-DMSO): δ=6.32 (s, 1H, CH), 3.49 (s, 2H, Ar—CH$_2$N), 2.19 (2, 6H, NCH$_3$), 2.08 (s, 3H, CH$_3$), 2.07 (s, 3H, CH$_3$).

GC-MS (ES) m/z: 195 [M$^+$], 150 [M$^+$+-dimethylamine], 122, 107, 46 [H$_2$NMe$_2^+$].

III) Hydrogenolysis of 2,6-dimethyl-3-morpholinomethyl-hydro-p-benzoquinone to 2,3,5-trimethyl-hydro-p-benzoquinone Example III.1

Hydrogenolysis of 2,6-dimethyl-3-morpholinomethyl-hydro-p-benzoquinone in tert.-butyl methyl ether A) In a 100-ml steel autoclave 3,5-dimethyl-2-morpholinomethyl-hydro-p-benzoquinone (3,5-DM-2-MHQ, 3.256 g, 91.1 wt %, 12.5 mmol) and a Pd/C (10%) catalyst (0.266 g, s/c 50) were suspended in 30 ml of methyl-tert.-butyl ether (MTBE) under a nitrogen atmosphere. After flushing with nitrogen three times, the autoclave was pressurized with hydrogen to 6 bara, then the pressure was released, and the mixture heated up to 160° C. during 30 minutes while stirring (gas dispersion stirrer, 1000 rpm). When the reaction temperature was reached, the autoclave was pressurized with 22 bara H$_2$. After 5 h, the catalyst was filtered off under exclusion of air by using a 0.45 μm membrane filter and washed with 6.5 ml of MTBE. The combined dark yellow ether layers were washed twice with aqueous 1 N HCl solution (40 ml) and once with H$_2$O (40 ml, resulting pH=2). The aqueous washings were re-extracted with MTBE (40 ml). The combined organic extracts were dried over Na$_2$SO$_4$, concentrated under reduced pressure (20 mbara) at 40° C. and further dried for 1 hour at room temperature to give 1.703 g off-white crystals which were analyzed by HPLC.

Yield according to quantitative HPLC: 82.3% TMHQ, 0.0% 3,5-DM-2-MHQ, 0.1% TMQ, 2.9% 2,6-DMHQ, 1.2% TetraMHQ.

B) To a 30-ml—steel autoclave 2,6-dimethyl-3-morpholinomethyl-hydro-p-benzoquinone (300 mg, 99%), methyl tert.-butyl ether (3 ml) and Pd/C (30 mg, 5% palladium) were added. The closed autoclave was agitated at 140° C. for 7 hours. The hydrogen pressure was initially set on 6 bara. For analysis purposes a small sample is silylated. According to GC-area % the yield of 2,3,5-trimethyl-hydro-p-benzoquinone is 93.5% (97.3% conversion), based on 2,6-dimethyl-hydro-p-benzoquinone.

Example III.2

Hydrogenolysis of 2,6-dimethyl-3-morpholinomethyl-hydro-p-benzoquinone in tert.-butyl ethyl ether Carrying out the experiment described in Example III.1 with tert.-butyl ethyl ether as the solvent (at 29 bara H$_2$, reaction time 4 h) in a 125-ml autoclave, the following results were obtained:

Yield: 67.0% TMHQ, 0.0% 3,5-DM-2-MHQ, 0.1% TMQ, 1.9% 2,6-DMHQ, 0.1% TetraMHQ.

Example III.3

Hydrogenolysis of 2,6-dimethyl-3-morpholinomethyl-hydro-p-benzoquinone in tert.-amyl methyl ether Carrying out the experiment described in Example III.1 with tert.-amyl methyl ether as the solvent (at 27 bara H$_2$, reaction time 4 h; no additional solvent used for washing the catalyst after filtration) in a 125-ml autoclave, the following results were obtained:

Yield: 80.1% TMHQ, 0.0% 3,5-DM-2-MHQ, 0.5% TMQ, 1.7% 2,6-DMHQ, 0.5% TetraMHQ.

Example III.4

Hydrogenolysis of 2,6-dimethyl-3-morpholinomethyl-hydro-p-benzoquinone in methoxycyclopentane Carrying out the experiment described in Example III.1 with methoxycyclopentane as the solvent (at 24 bara $H_2$, reaction time 4 h; no additional solvent used for washing the catalyst after filtration) in a 125-ml autoclave, the following results were obtained:

Yield: 82.5% TMHQ, 0.0% 3,5-DM-2-MHQ, 0.1% TMQ, 1.5% 2,6-DMHQ, 0.1% TetraMHQ.

Example III.5-III.14

Hydrogenolysis of 2,6-dimethyl-3-morpholinomethyl-hydro-p-benzoquinone in tert.-butyl methyl ether with different catalysts In a steel autoclave were methyl tert.-butyl ether, 2,6-dimethyl-3-morpholinomethyl-hydro-p-benzoquinone (10 weight % in methyl tert.-butyl ether) and catalyst (10-50 weight % based on 2,6-dimethyl-3-morpholinomethyl-hydro-p-benzoquinone) added. The closed autoclave was agitated (250 rpm) at 120-160° C. for 7 hours. The hydrogen pressure was initially set on 6-11 bara. For analysis a small probe was silylated. In the table below the results are summarized (based on GC-area %="A %").

TABLE 5

Hydrogenolysis of 3,5-DM-2-MHQ to TMHQ

| Example | Catalyst [type] | s/c | $H_2$ Pressure [bara] | Temperature [° C.] | Yield [A %] | Conversion [A %] | Selectivity [A %] |
|---|---|---|---|---|---|---|---|
| III.5 | 5% Pd/C | 90 | 6 | 140 | 93 | 97 | 96 |
| III.6 | 5% Pd/C | 90 | 6 | 160 | 91 | 100 | 91 |
| III.7 | 5% Pd/C | 90 | 11 | 140 | 94 | 99 | 95 |
| III.8 | 10% Pd/C - egg-shell catalyst | 90 | 6 | 140 | 88 | 92 | 96 |
| III.9 | 5% Pd/SiO$_2$ | 90 | 6 | 140 | 66 | 69 | 96 |
| III.10 | 5% Pd/SiO$_2$ | 90 | 11 | 140 | 71 | 74 | 95 |
| III.11 | 1% Pd/TP | 673 | 11 | 160 | 92 | 99 | 92 |
| III.12 | 1% Pd/TP | 90 | 11 | 140 | 90 | 98 | 92 |
| III.13 | 5% Pd/CaCO$_3$ | 45 | 6 | 140 | 59 | 59 | 99 |
| III.14 | Ni alloy | 1.2 | 11 | 140 | 58 | 60 | 98 |

The invention claimed is:

1. A process for the manufacture of 2,3,5-trimethyl-hydro-p-benzoquinone comprising the following steps:
   a) hydrogenating 2,6-dimethyl-p-benzoquinone with hydrogen in the presence of a hydrogenation catalyst in an organic solvent to obtain 2,6-dimethyl-hydro-p-benzoquinone;
   b) reacting 2,6-dimethyl-hydro-p-benzoquinone with a secondary amine and formaldehyde in an organic solvent to obtain 2,6-dimethyl-3-(N,N-disubstituted aminomethyl)-hydro-p-benzoquinone;
   c) reacting 2,6-dimethyl-3-(N,N-disubstituted aminomethyl)-hydro-p-benzoquinone with hydrogen in the presence of a hydrogenolysis catalyst in an organic solvent to obtain 2,3,5-trimethylhydro-p-benzoquinone; wherein
   the organic solvent used in steps a), b) and c) is independently selected from the group consisting of methyl tert.-butyl ether, ethyl tert.-butyl ether, methyl tert.-amyl ether, methoxycyclopentane and any mixtures thereof.

2. The process according to claim 1, wherein the organic solvent in all steps a), b) and c) is the same.

3. The process according to claim 1, wherein the organic solvent used in all steps a), b) and c) is methyl tert.-butyl ether.

4. The process according to claim 1, wherein the catalyst used in step c) is selected from the group consisting of Pd/C, Pd/SiO$_2$, Pd/Al$_2$O$_3$, Pd/porous glass and Ni alloy.

5. The process according to claim 1, wherein the formaldehyde used in step b) is used in form of formalin.

6. The process according to claim 1, wherein the secondary amine used in step b) is a N,N-disubstituted amine L-N(H)-L$^1$, where L and L$^1$ are independently from each other selected from the group consisting of aliphatic linear alkyl groups which may optionally contain heteroatoms, aliphatic branched alkyl groups which may optionally contain heteroatoms, single or multiple unsaturated linear alk(mono-/oligo-/poly)enyl groups which may optionally contain heteroatoms, and single or multiple unsaturated branched alk(mono-/oligo-/poly)enyl groups which may optionally contain heteroatoms, or L and L$^1$ may form an aliphatic N-containing cycloalkane or an aromatic N-containing heterocycle which may optionally contain further heteroatoms.

7. A process for the manufacture of 2,3,5-trimethyl-hydro-p-benzoquinone comprising the step of reacting 2,6-dimethyl-3-(N,N-disubstituted aminomethyl)-hydro-p-benzoquinone with hydrogen in the presence of a hydrogenolysis catalyst in an organic solvent to obtain 2,3,5-trimethyl-hydro-p-benzoquinone, wherein the organic solvent is selected from the group consisting of methyl tert.-butyl ether, ethyl tert.-butyl ether, methyl tert.-amyl ether, methoxycyclopentane and any mixtures thereof.

8. A process for the manufacture of 2,3,5-trimethylhydro-p-benzoquinone comprising the following steps:
   i) reacting 2,6-dimethyl-hydro-p-benzoquinone with a secondary amine and formaldehyde in an organic solvent to obtain 2,6-dimethyl-3-(N,N-disubstituted aminomethyl)-hydro-p-benzoquinone;
   ii) reacting 2,6-dimethyl-3-(N,N-disubstituted aminomethyl)-hydro-p-benzoquinone with hydrogen in the presence of a hydrogenolysis catalyst in an organic solvent to obtain 2,3,5-trimethyl-hydro-p-benzoquinone, wherein the organic solvent used in steps i) and ii) is independently selected from the group consisting of methyl tert.-butyl ether, ethyl tert.-butyl ether, methyl tert.-amyl ether, methoxycyclopentane and any mixtures thereof.

9. A process for the manufacture of 2,6-dimethyl-3-(N,N-disubstituted aminomethyl)-hydro-p-benzoquinone comprising the step of reacting 2,6-dimethyl-hydro-p-benzoquinone with a secondary amine and formaldehyde in an organic solvent to obtain 2,6-dimethyl-3-(N,N-disubstituted aminomethyl)-hydro-p-benzoquinone, wherein the organic solvent is selected from the group consisting of methyl tert.-butyl ether, ethyl tert.-butyl ether, methyl tert.-amyl ether, methoxycyclopentane and any mixtures thereof.

10. A process for the manufacture of 2,6-dimethyl-3-(N,N-disubstituted aminomethyl)-hydro-p-benzoquinone comprising the following steps:

hydrogenating 2,6-dimethyl-p-benzoquinone with hydrogen in the presence of a hydrogenation catalyst in an organic solvent to obtain 2,6-dimethyl-hydro-p-benzoquinone;

reacting 2,6-dimethyl-hydro-p-benzoquinone with a secondary amine and formaldehyde in an organic solvent to obtain 2,6-dimethyl-3-(N,N-disubstituted aminomethyl)-hydro-p-benzoquinone; wherein the organic solvent in both steps is independently selected from the group consisting of methyl tert.-butyl ether, ethyl tert.-butyl ether, methyl tert.-amyl ether, methoxycyclopentane and any mixtures thereof.

11. A process for the manufacture of 2,6-dimethyl-hydro-p-benzoquinone comprising the step of hydrogenating 2,6-dimethyl-p-benzoquinone with hydrogen in the presence of a hydrogenation catalyst in an organic solvent, wherein the organic solvent is selected from the group consisting of methyl tert.-butyl ether, ethyl tert.-butyl ether, methyl tert.-amyl ether, methoxycyclopentane and any mixtures thereof.

12. The process according to claim 6, wherein the heteroatoms are selected from O and N.

13. The process according to claim 6, wherein the secondary amine used in step b) is selected from the group consisting of dimethyl amine, diethyl amine, di-n-propyl amine, diethanol amine, piperidine, 1-methyl-piperazine, pyrrolidine and morpholine.

14. The process according to claim 6, wherein the secondary amine used in step b) is morpholine.

15. The process according to claim 7, wherein the 2,6-dimethyl-3-(N,N-disubstituted aminomethyl)-hydro-p-benzoquinone is 2,6-dimethyl-3-morpholinomethyl-hydro-p-benzoquinone.

16. The process according to claim 8, wherein the secondary amine is morpholine, and wherein the 2,6-dimethyl-3-(N,N-disubstituted aminomethyl)-hydro-p-benzoquinone is 2,6-dimethyl-3-morpholinomethyl-hydro-p-benzoquinone.

17. The process according to claim 9, wherein the 2,6-dimethyl-3-(N,N-disubstituted aminomethyl)-hydro-p-benzoquinone is 2,6-dimethyl-3-morpholinomethyl-hydro-p-benzoquinone, the secondary amine is morpholine, and the 2,6-dimethyl-3-(N,N-disubstituted aminomethyl)-hydro-p-benzoquinone is 2,6-dimethyl-3-morpholinomethyl-hydro-p-benzoquinone.

18. The process according to claim 10, wherein the 2,6-dimethyl-3-(N,N-disubstituted aminomethyl)-hydro-p-benzoquinone is 2,6-dimethyl-3-morpholinomethyl-hydro-p-benzoquinone, the secondary amine is morpholine, and the 2,6-dimethyl-3-(N,N-disubstituted aminomethyl)-hydro-p-benzoquinone is 2,6-dimethyl-3-morpholinomethyl-hydro-p-benzoquinone.

19. A process for the manufacture of vitamin E comprising at least one of the steps a) to c) according to claim 1 to obtain 2,3,5-trimethyl-hydro-p-benzoquinone, and further reacting the 2,3,5-trimethyl-hydro-p-benzoquinone with isophytol and/or phytol and/or derivatives of isophytol or phytol to obtain vitamin E.

20. A process for the manufacture of vitamin E acetate comprising at least one of the steps a) to c) according to claim 1 to obtain 2,3,5-trimethyl-hydro-p-benzoquinone, converting the 2,3,5-trimethyl-hydro-p-benzoquinone to 2,3,5-trimethyl-hydro-p-benzoquinone acetate, and thereafter reacting the 2,3,5-trimethyl-hydro-p-benzoquinone acetate with isophytol and/or phytol and/or derivatives of isophytol or phytol to obtain vitamin E.

21. Compounds selected from the group consisting of the Mannich adduct of 2,6-dimethyl-hydro-p-benzoquinone with diethyl amine, di-n-propyl amine, diethanol amine, piperidine, 1-methyl-piperazine and pyrrolidine.

* * * * *